United States Patent
Coret

(10) Patent No.: US 7,329,770 B2
(45) Date of Patent: Feb. 12, 2008

(54) ESTERS AS USEFUL BROAD SPECTRUM HERBICIDAL COMPOUNDS

(76) Inventor: Joel Marcel Coret, 135 Castleton Rd., Princeton, NJ (US) 08540

( * ) Notice: Subject to any disclaimer, the term of this patent is extended or adjusted under 35 U.S.C. 154(b) by 101 days.

(21) Appl. No.: 11/156,853

(22) Filed: Jun. 20, 2005

(65) Prior Publication Data

US 2005/0282706 A1 Dec. 22, 2005

Related U.S. Application Data

(66) Substitute for application No. 60/581,661, filed on Jun. 21, 2004.

(60) Provisional application No. 60/581,639, filed on Jun. 21, 2004, provisional application No. 60/581,641, filed on Jun. 21, 2004, provisional application No. 60/581,638, filed on Jun. 21, 2004.

(51) Int. Cl.
| | |
|---|---|
| *C07C 69/76* | (2006.01) |
| *C07D 237/26* | (2006.01) |
| *C07D 211/72* | (2006.01) |
| *C07D 263/58* | (2006.01) |
| *A01N 43/00* | (2006.01) |
| *A01N 37/00* | (2006.01) |

(52) U.S. Cl. .......... 560/8; 544/235; 546/290; 548/221; 504/209; 504/307

(58) Field of Classification Search .......... 560/61, 560/62; 514/543
See application file for complete search history.

(56) References Cited

U.S. PATENT DOCUMENTS 5,012,017 A * 4/1991 Orvik et al. .......... 568/803

OTHER PUBLICATIONS

Li et al, CA 143:153157, Dec. 2004.*
Moedritzer et al., caplus an 1989:423509.*

* cited by examiner

*Primary Examiner*—Rebecca Anderson
*Assistant Examiner*—Sun Jae Y Loewe
(74) *Attorney, Agent, or Firm*—John A. Shedden

(57) ABSTRACT

The instant invention relates to the discovery of certain novel herbicidal esters of agriculturally active acids. These esters present agronomical advantages over traditional herbicidal products by presenting multiple herbicidal mechanisms that ensure activity over a broad weed spectrum while limiting the appearance of plant resistance.

4 Claims, No Drawings

ESTERS AS USEFUL BROAD SPECTRUM HERBICIDAL COMPOUNDS

The present invention claims the benefits accorded under 35 U.S.C. 119(e) of prior provisional application Nos. 60/581,661; 60/581,639; 60/581,641; and 60/581,638: all filed on 21 Jun. 2004.

FIELD OF THE INVENTION

The instant invention relates to novel herbicidal ester compounds and the discovery that compositions containing these compounds can present many agronomical advantages over the use of traditional products.

BACKGROUND OF THE INVENTION

Pesticides are widely regarded as an efficient way of optimizing agricultural production by reducing the pressure from pests and other organisms on the growing crops. Both the quantity and the quality of crops are increased by use of chemical compounds that reduce damage to the crop by insects, fungi or weeds.

In order to reduce the pressure of competitive vegetation on the crop, herbicides have proven effective in limiting growth of unwanted plants. The herbicidal compounds can either kill all or most vegetation that they come into contact with (total or unselective herbicides) or can selectively affect certain types of plants while barely affecting others. This is particularly helpful when a crop is unharmed by a compound whereas a broad spectrum of unwanted weeds are killed by the same compound—the compound is then said to be selective with respect to the crop and can be applied to the agricultural area even after the crop has started to grow, i.e., post-emergent. This is helpful when an herbicidal treatment is required during the growing season to control high weed pressure. Very often, weeds that spontaneously appear represent a large number of different species that react differently to herbicides. To ensure optimal control, it is common practice to apply more than one herbicidal compound in the course of a season over agricultural areas. This also reduces the probability of plants developing a resistance to any given herbicide, since different herbicides usually affect different cellular targets in the plant and so a resistant plant would need to simultaneously develop more than one mechanism or mutation (one for each herbicide applied) in order to survive and reproduce. However, this multiple application increases the cost of control for the farmer, both in costs of products, and also in labor and application times when products are applied consecutively. It has been found, and is an object of this invention, that novel ester compounds formed from acids and alcohols that present herbicidal properties present excellent herbicidal properties toward broad-leafed weed species as well as grasses. Some of these novel esters can be useful in eliminating weeds that have become tolerant of either the precursor alcohol or acid.

SUMMARY OF THE INVENTION

The present invention relates to the discovery of certain novel herbicidal ester compounds that are generally composed of one or more herbicidal acid groups esterified onto a range of herbicidal alcohols.

DETAILED DESCRIPTION OF THE INVENTION

The present invention thus relates to novel herbicidal ester compounds. These compounds are composed of one or more herbicidal acid groups esterified onto a range of herbicidal alcohols.

Examples of novel compounds that present these characteristics and which are considered to be covered by present invention are:

R—CO—O—R'     (I)

where R—CO—O represents an acetate of one of the following acids: arylalanines such as
N-benzoyl-N-(3,4-dichlorophenyl)-DL-alanine(benzoylprop), and
N-benzoyl-N-(3-chloro-4-fluorophenyl)-D-alanine(flamprop); aryloxyphenoxypropionic acids such as
(RS)-2-[4-(3,5-dichloro-2-pyridyloxy)phenoxy]propionic acid (chlorazifop),
(R)-2-[4-(5-chloro-3-fluoro-2-pyridyloxy)phenoxy]propionic acid (clodinafop),
(RS)-2-[4-(4-chlorophenoxy)phenoxy]propionic acid (clofop),
(R)-2-[4-(4-cyano-2-fluorophenoxy)phenoxy]propionic acid (cyhalofop),
(RS)-2-[4-(2,4-dichlorophenoxy)phenoxy]propionic acid (diclofop),
(RS)-2-[4-(6-chloro-1,3-benzoxazol-2-yloxy)phenoxy]propionic acid (fenoxaprop),
(R)-2-[4-(6-chloro-1,3-benzoxazol-2-yloxy)phenoxy]propionic acid (fenoxaprop-P),
(RS)-2-[4-(5-trifluoromethyl-2-pyridyloxy)phenoxy]propionic acid (fluazifop),
(R)-2-[4-(5-trifluoromethyl-2-pyridyloxy)phenoxy]propionic acid (fluazifop-P),
(RS)-2-[4-(3-chloro-5-trifluoromethyl-2-pyridyloxy)phenoxy]propionic acid (haloxyfop),
(RS)-2-{4-[3-chloro-5-(trifluoromethyl)-2-pyridyloxy]phenoxy}propionic acid (haloxyfop),
(RS)-2-[4-(6-chloroquinoxalin-2-yloxy)phenoxy]propionic acid (quizalofop),
(R)-2-[4-(6-chloroquinoxalin-2-yloxy)phenoxy]propionic acid (quizalofop-P), and
(RS)-2-[4-(α,α,α-trifluoro-p-tolyloxy)phenoxy]propionic acid (trifop); benzoic acids such as
3-amino-2,5-dichlorobenzoic acid (chloramben),
3,6-dichloro-o-anisic acid (dicamba), and
3,5,6-trichloro-o-anisic acid (tricamba); cyclohexene oximes such as
(E)-(RS)-3-[1-(allyloxyimino)butyl]-4-hydroxy-6,6-dimethyl-2-oxocyclohex-3-enecarboxylic acid (alloxydim); dicarboximides such as
(RS)-2-(5-ethyl-2-{4-[1,2,3,6-tetrahydro-3-methyl-2,6-dioxo-4-(trifluoromethyl)pyrimidin-1-yl]phenoxymethyl}phenoxy)propionic acid (benzfendizone),
(Z)-2-chloro-3-[2-chloro-5-(cyclohex-1-ene-1,2-dicarboximido)phenyl]acrylic acid (cinidon), and
[2-chloro-5-(cyclohex-1-ene-1,2-dicarboximido)-4-fluorophenoxy]acetic acid (flumiclorac); imidazolinones such as
2-[4,5-dihydro-4-methyl-4-(1-methylethyl)-5-oxo-1H-imidazol-2-yl]-4(or 5)-methylbenzoic acid (imazamethabenz),
(RS)-2-(4-isopropyl-4-methyl-5-oxo-2-imidazolin-2-yl)-5-methoxymethylnicotinic acid (imazamox),
(RS)-2-(4-isopropyl-4-methyl-5-oxo-2-imidazolin-2-yl)-5-methylnicotinic acid (imazapic),
2-(4-isopropyl-4-methyl-5-oxo-2-imidazolin-2-yl)nicotinic acid (imazapyr)
(RS)-2-(4-isopropyl-4-methyl-5-oxo-2-imidazolin-2-yl)quinoline-3-carboxylic acid (imazaquin), and (RS)-5-ethyl-2-(4-isopropyl-4-methyl-5-oxo-2-imidazolin-2-yl)nicotinic acid (imazethapyr); nitrophenyl ethers such as
5-(2-chloro-α,α,α-trifluoro-p-tolyloxy)-2-nitrobenzoic acid (acifluorfen),
5-(2,4-dichlorophenoxy)-2-nitrobenzoic acid (bifenox),
O-[5-(2-chloro-α,α,α-trifluoro-p-tolyloxy)-2-nitrobenzoyl] glycolic acid (fluoroglycofen), and
O-[5-(2-chloro-α,α,α-trifluoro-p-tolyloxy)-2-nitrobenzoyl]-DL-lactic acid (lactofen); phenoxyacetic acids such as
(2,4-dichlorophenoxy)acetic acid (2,4-D),
4-chlorophenoxyacetic acid (4-CPA), and
(4-chloro-2-methylphenoxy)acetic acid (mcpa); phenoxybutyric acids such as
4-(2,4-dichlorophenoxy)butyric acid (2,4-DB), and
4-(4-chloro-o-tolyloxy)butyric acid (mcpb); phenoxypropionic acids such as
(RS)-2-(3-chlorophenoxy)propionic acid (cloprop),
(RS)-2-(2,4-dichlorophenoxy)propionic acid (dichlorprop),
(R)-2-(2,4-dichlorophenoxy)propionic acid (dichlorprop-P),
(RS)-2-(4-chloro-o-tolyloxy)propionic acid (mecoprop), and
(R)-2-(4-chloro-o-tolyloxy)propionic acid (mecoprop-P); picolinic acids such as
4-amino-3,6-dichloropyridine-2-carboxylic acid (aminopyralid),
3,6-dichloropyridine-2-carboxylic acid (clopyralid),
4amino-3,5-dichloro-6-fluoro-2-pyridyloxyacetic acid (fluroxypyr), and
4-amino-3,5,6-trichloropyridine-2-carboxylic acid (picloram); pyrazolphenyls such as
5-[4-bromo-1-methyl-5-(trifluoromethyl)pyrazol-3-yl]-2-chloro-4-fluorobenzoic acid (fluazolate), and
2-chloro-5-(4-chloro-5-difluoromethoxy-1-methylpyrazol-3-yl)-4-fluorophenoxyacetic acid (pyraflufen); pyridazinones such as
2-chloro-5-[1,6-dihydro-5-methyl-6-oxo-4-(trifluoromethyl)pyridazin-1-yl]-4-fluorophenoxyacetic acid (flufenpyr),
5-bromo-1,6-dihydro-6-oxo-1-phenylpyridazin-4-yloxamic acid (oxapyrazon), and
(RS)-hexahydro-4-hydroxy-3,6-dioxopyridazin-4-ylacetic acid (pydanon); pyridines such as
2-difluoromethyl-5-(4,5-dihydro-1,3-thiazol-2-yl)-4-isobutyl-6-trifluoromethylnicotinic acid (thiazopyr), and
3,5,6-trichloro-2-pyridyloxyacetic acid (Triclopyr); pyrimidinyloxybenzoics such as
2,6-bis(4,6-dimethoxypyrimidin-2-yloxy)benzoic acid (Bispyribac), and
2-(4,6-dimethoxypyrimidin-2-yloxy)-6-(1-methoxyiminoethyl)benzoic acid (Pyriminobac);

pyrimidinylthiobenzoic acids such as
2-chloro-6-(4,6-dimethoxypyrimidin-2-ylthio)benzoic acid (pyrithiobac);

quinolinecarboxylics such as
3,7-dichloroquinoline-8-carboxylic acid (Quinclorac), and
7-chloro-3-methylquinoline-8-carboxylic acid (Quinmerac);

sulfonanilides such as
3-chloro-2-(5-ethoxy-7-fluoro[1,2,4]triazolo[1,5-c]pyrimidin-2-ylsulfonamido)benzoic acid (Cloransulam);

triazolones such as
(RS)-2-chloro-3-{2-chloro-5-[4-(difluoromethyl)-4,5-dihydro-3-methyl-5-oxo-1H-1,2,4-triazol-1-yl]-4-fluorophenyl}propionic acid (Carfentrazone);

unclassified such as
[2-chloro-4-fluoro-5-(5,6,7,8-tetrahydro-3-oxo-1H,3H-[1,3,4]thiadiazolo[3,4-a]pyridazin-1-ylideneamino)phenylthio]acetic acid (Fluthiacet);

uracils such as
1-(allyloxycarbonyl)-1-methylethyl 2-chloro-5-[1,2,3,6-tetrahydro-3-methyl-2,6-dioxo-4-(trifluoromethyl)pyrimidin-1-yl]benzoic acid (Butafenacil), and
2-chloro-5-(1,2,3,6-tetrahydro-3-methyl-2,6-dioxo-4-trifluoromethylpyrimidin-1-yl)benzoic acid (flupropasil);

Phosphonic acid derivatives such as
N-(phosphonomethyl)glycine(glyphosate) and the salts thereof;

Phosphinic acid derivatives such as
4-[hydroxyl(methyl)phosphinoyl]-DL-homoalanine(glufosinate) and the salts thereof;

Sulfonylurea derivatives such as
3-chloro-5-(4,6-dimethoxypyrimidin-2-ylcarbamoylsulfamoyl-1-methylpyrazole carboxylic acid (Halosulfuron) EP-A0282613,
3-[(4,6-dimethoxypyrimidin-2-ylcarbamoyl)sulfamoyl]-6-(trifluoromethyl)nicotinic acid (Flupyrsulfuron) see Brighton Crop Prot. Conf. Weeds, 1995, p. 49),
2-[[[[(4,6-dimethoxy-2-pyrimidinyl)amino]carbonyl]amino]sulfonyl]-4-[[(methylsulfonyl)amino]methyl]benzoic acid (Mesosulfuron),
2-[4,6-bis(difluoromethoxy)pyrimidin-2-ylcarbamoylsulfamoyl]benzoic acid (Primisulfuron),
5-[(4,6-dimethoxypyrimidin-2-ylcarbamoyl)sulfamoyl]-1-methylpyrazole-4-carboxylic acid (Pyrazosulfuron),
3-chloro-5-(4,6-dimethoxypyrimidin-2-ylcarbamoylsulfamoyl)-1-methylpyrazole-4-carboxylic acid (EP-A 0 282 613),
5-(4,6-dimethylpyrimidin-2-yl-carbamoylsulfamoyl)-1-(2-pyrid-yl)pyrazole-4-carboxylic acid (NC-330, see Brighton Crop Prot. Conference 'Weeds' 1991, Vol. 1, p45 et seq.),
3-chloro-2-(5-ethoxy-7-fluoro[1,2,4]triazolo[1,5-c]pyrimidin-2-ylsulfonamido)benzoic acid (Cloransulam),
2-[(4-ethoxy-6-methylamino-1,3,5-triazin-2-yl)carbamoyl-sulfamoyl]benzoic acid (Ethametsulfuron),
4-iodo-2-[3-(4-methoxy-6-methyl-1,3,5-triazin-2-yl)ureidosulfonyl]benzoic acid (Iodosulfuron) W092/13845,
3-(4-methoxy-6-methyl-1,3,5-triazin-2-ylcarbamoylsulfamoyl)thiophene-2-carboxylic acid (Thifensulfuron),
2-[4-methoxy-6-methyl-1,3,5-triazin-2-yl(methyl)carbamoylsulfamoyl]benzoic acid (Tribenuron),
2-[4-dimethylamino-6-(2,2,2-trifluoroethoxy)-1,3,5-triazin-2-ylcarbamoylsulfamoyl]-m-toluic acid (Triflusulfuron), and
3-(4-ethyl-6-methoxy-1,3,5-triazin-2-yl)-1-(2,3-dihydro-1,1-dioxo-2-methylbenzo[b]thiophen-7-sulfonyl)urea (EP-A 0 796 83); and urea derivatives such as
2-{1-[4-(3,5-difluorophenyl)semicarbazono]ethyl}nicotinic acid (diflufenzopyr);

and R' is the corresponding alkyl group of an alcohol selected from the group consisting of:
methyl (E)-(RS)-3-[1-(allyloxyimino)butyl]-4-hydroxy-6,6-dimethyl-2-oxocyclohex-3-enecarboxylate,
(RS)-(EZ)-5-(3-butyryl-2,4,6-trimethylphenyl)-2-(1-ethoxyiminopropyl)-3-hydroxycyclohex-2-en-1-one,
(RS)-2-[(E)-1-[(E)-3-chloroallyloxyimino]propyl]-5-[2-(ethylthio)propyl]-3-hydroxycyclohex-2-en-1-one, (RS)-(EZ)-2-[1-(3-chloroallyloxy)iminobutyl]-5-(2-ethylthiopropyl)-3-hydroxycyclohex-2-en-1-one,
(RS)-(EZ)-2-[1-(ethoxyimino)butyl]-3-hydroxy-5-thian-3-ylcyclohex-2-en-1-one,
2-{(EZ)-1-[(2RS)-2-(4-chlorophenoxy)propoxyimino]butyl}-3-hydroxy-5-(thian-3-yl)cyclohex-2-en-1-one,
6-chloro-3-phenylpyridazin-4-ol,
(RS)-(EZ)-2-(1-ethoxyiminobutyl)-5-[2-(ethylthio)propyl]-3-hydroxycyclohex-2-en-1-one,
(RS)-(EZ)-2-{1-[(2E)-3-chloroallyloxyimino]propyl}-3-hydroxy-5-perhydropyran-4-ylcyclohex-2-en-1-one,
(RS)-(EZ)-2-[1-(ethoxyimino)propyl]-3-hydroxy-5-mesitylcyclohex-2-en-1-one,
4-hydroxy-3,5-di-iodobenzonitrile,
3,5-dibromo-4-hydroxybenzonitrile,
3,5-dichloro-4-hydroxybenzonitrile,
3,5-dichloro-2,6-difluoropyridin-4-ol,
2,3,5-trichloropyridin-4-ol, and
6-chloro-3-phenylpyridazin-4-ol.

Among the most preferred esters is where the RCOO group is

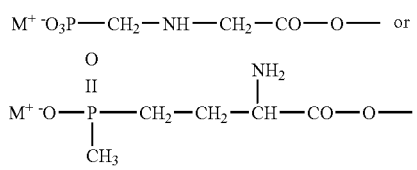

wherein M$^+$ is an agronomically acceptable cation such as sodium, potassium, ammonium, alkylamines, dialkylamines, alkanolamines, or trimethylsulfonium.

These esters can be prepared by an esterification reaction which can be carried out according to classical methods. Acids, acid halides or light alkyl esters thereof (methyl esters, for example) are progressively added to the alcohol in the presence of an appropriate catalyst (usually an acid such as toluene sulfonic acid) in a high temperature reactor under agitation. The reaction can be improved by a continuous extraction of by-products (water or light alcohol if a light ester is used as reactant) as is commonly practiced by those familiar to the art of organic synthesis.

If necessary, the use of a polar, non-protic solvent or plasticizer will be beneficial in solubilizing the reactants or in reducing the viscosity of the reactive solution.

The active ingredients are normally formulated into herbicidal compositions that ensure appropriate handling characteristics and dispersibility of the active(s) in order to optimize delivery of the active(s) to the locus of application.

The herbicidal compositions according to the invention conventionally comprise from about 0.0001 to 99% by weight, preferably 0.1 to 95% by weight, of one or more herbicidal active substances.

The herbicidal compositions according to the invention present excellent herbicidal activity. The improved control of the harmful plants by the herbicidal compositions according to the invention makes it possible to reduce the application rate and/or to increase the safety margin. This is an improvement both from the economic and the environmental point of view.

The herbicidal compositions according to the invention are prepared by customary formulation processes, for example grinding, mixing, dissolving or dispersing individual components.

The herbicidal compositions according to the invention can be formulated in various ways, depending on the prevailing biological and/or chemical-physical parameters. The following are examples of suitable formulation possibilities: soluble concentrates (SL), wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing materials, granules for spreading and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Kuchler, "Chemische Technologie" [Chemical Engineering], Volume 7, C. Hauser Verlag Munich, 4.sup.th Ed. 1986; Wade van Valkenburg, "Pesticide Formulations", Marcel Dekker, N.Y., 1973; and K. Martens, "Spray Drying" Handbook, 3rd Ed. 1979, G. Goodwin Ltd. London.

The formulation auxiliaries required, such as inert materials, surfactants, solvents and additives, are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell., Stuttgart 1976; and Winnacker-Kuchler, "Chemische Technologie", Volume 7, C. Hauser Verlag Munich, 4.sup.th Ed. 1986.

Based on these formulations, it is also possible to prepare combinations with other agrochemical active substances such as insecticides, acaricides, safeners, fertilizers and/or growth regulators, for example in the form of a readymix or a tank mix.

Wettable powders are products which are uniformly dispersible in water and which, besides the herbicide and/or surfactant, also comprise diluents or inert materials and, if appropriate, further ionic and/or nonionic surfactants (wetters, dispersants, etc.), for example polyalkoxyylated arylphenols, polyalkoxylated alkylphenols, polyalkoxylated fatty alcohols, polyalkoxylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutyinaphthalene sulfonate or sodium oleoylmethyltaurine. To prepare the wettable powders, the herbicides and/or surfactants are finely ground, for example in customary apparatuses such as hammer mills, blower mills and/or air-jet mills, and mixed with the formulation auxiliaries, either simultaneously or subsequently. Emulsifiable concentrates are prepared by dissolving herbicide and/or surfactants in an organic solvent, for example butanol, cyclohexanone, dimethylformamide, xylene, glycols, methyl esters of natural fatty acids or else higher-boiling aromatics or hydrocarbons or mixtures of the organic solvents with addition of one or more ionic or nonionic surfactants (emulsifiers). Examples of emulsifiers which may be used are: calcium salts of alkylarylsulfonic acid, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters, or polyoxyethylene sorbitan esters such as, for example, polyoxyethylene sorbitan fatty acid esters. For the herbicidal actives that contain a hydrophilic alcohol representing at least 30% of the total molecular weight of the molecule, the dispersing qualities are found to be inherently suitable, which will reduce the need for the additional surfactants given as examples here.

Dusts are obtained by grinding herbicide and/or surfactant with finely divided solid materials, for example talc, natural clays such as kaolin, bentonite and pyrophyllite, or diatomaceous earth.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types. The stability of esters in water may be a concern, in which case the pH of the solution needs to be maintained between 6 and 7.5 to minimize hydrolytic degradation. Additionally, reductive agents can be added to the solution, or additional alcohols or polyols can be added to the solution.

Granules can be prepared either by spraying the herbicide and/or surfactants onto adsorptive, granulated inert material or by applying active ingredient concentrates to the surface of carriers such as sand, kaolinites or granulated inert material with the aid of adhesives, for example polyvinyl alcohol, sodium polyacrylate or else mineral oils. Suitable herbicide may also be granulated in the manner conventionally used for the production of fertilizer granules, if desired in a mixture with fertilizers. As a rule, water-dispersible granules are prepared by conventional processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd Ed. 1979, G. Goodwin Ltd., London; J. E. Browning, "Agglomeration", Chemical and Engineering 1967, page 147 et seq; and "Perry's Chemical Engineer's Handbook", 5th Ed., McGraw-Hill, New York 1973, pp. 8-57.

For further details on the formulation of crop protection products, see, for example, G. C. Klingman, "Weed Control as a Science", John Wiley and Sons, Inc., New York, 1961, pages 81-96; and J. D. Freyer, S. A. Evans, "Weed Control Handbook", 5th Ed., Blackwell Scientific Publications, Oxford, 1968, pages 101-103.

In addition, the abovementioned active ingredient formulations may comprise, if appropriate, additives such as adhesives, wetters, dispersants, emulsifiers, penetrants, preservatives, antifreeze agents, solvents, fillers, carriers, colorants, antifoams, evaporation inhibitors, pH regulators or viscosity regulators which are customary in each case.

The spray mixture is preferably prepared on the basis of water and/or an oil, for example a high-boiling hydrocarbon such as kerosene or paraffin. The herbicidal compositions according to the invention can be formulated as a tank mix or a readymix.

The active ingredient concentration in wettable powders is, for example, approximately 10 to 90% by weight, the remainder to 100% by weight being composed of customary formulation constituents. In the case of emulsifiable concentrates, the active ingredient concentration may amount to approximately 1 to 90%, preferably 5 to 80% by weight. Formulations in the form of dusts comprise 1 to 30% by weight of active ingredient, preferably in most cases 5 to 20% by weight of active ingredient; and sprayable solutions contain approximately 0.05 to 80%, preferably 2 to 50% by weight of active ingredient. In the case of water-dispersible granules, the active ingredient content depends partly on whether the active compound is present in liquid or solid form and on which granulation auxiliaries, fillers and the like are being used. The active ingredient content amounts to, for example, between 1 and 95% by weight, preferably to between 10 and 80% by weight in the case of the water-dispersible granules.

Upon application, the concentration of the herbicide is generally 0.0001 to 20% by weight, preferably 0.01 to 3% by weight, in the composition applied, for example the spray mixture, at an application rate of 5 to 4000 l/ha, preferably 100 to 600 l/ha.

Preferably, the herbicidal compositions according to the invention additionally comprise water and if appropriate, organic solvents and are formulated in the form of an aqueous concentrated dispersion or emulsion or as a tank mix in the form of a dilute dispersion, emulsion or solution with a degree of dilution of up to that of the ready-to-use spray mixture. A herbicidal composition prepared as a tank mix and comprising, for use, the preferred amounts of herbicide, is especially preferred.

Mixtures or co-formulations with other active substances such as, for example, insecticides, acaricides, herbicides, fungicides, safeners, fertilizers and/or growth regulators are possible, if appropriate.

For use, concentrated formulations which are present in commercially available form are, if appropriate, diluted in the customary fashion, for example by means of water in the case of wettable powders, emulsifiable concentrates, dispersions and water-dispersible granules. Preparations in the form of dusts, spray granules, absorption granules, sprayable solutions and spray mixtures prepared as tank mixes are not conventionally diluted further with additional inert substances prior to use.

The application rate required of the herbicides varies with the external conditions such as temperature, humidity and the nature of the herbicide used. It can vary within wide limits, for example between 0.001 and 10 kg/ha or more of active substance, but it is preferably between 0.005 and 5 kg/ha.

The herbicidal compositions according to the invention have an outstanding herbicidal activity against monocotyledonous and dicotyledonous weeds, and as such, will be active against many crop plants. However, by choosing suitable herbicidal acids and alcohols, it is possible to produce esters that are selective to certain economically important crops.

For example, soybeans will be more resistant to mixed esters based on combinations of the following acids:
(RS)-2-(4-isopropyl-4-methyl-5-oxo-2-imidazolin-2-yl)-5-methoxymethylnicotinic acid,
(RS)-2-(4-isopropyl-4-methyl-5-oxo-2-imidazolin-2-yl) quinoline-3-carboxylic acid,
(RS)-5-ethyl-2-(4-isopropyl-4-methyl-5-oxo-2-imidazolin-2-yl)nicotinic acid, and
(RS)-2-[4-(5-trifluoromethyl-2-pyridyloxy)phenoxy]propionic acid; And alcohols:
(RS)-(EZ)-2-[1-(ethoxyimino)butyl]-3-hydroxy-5-thian-3-ylcyclohex-2-en-1-one, and
(RS)-2-[(E)-1-[(E)-3-chloroallyloxyimino]propyl]-5-[2-(ethylthio)propyl]-3-hydroxycyclohex-2-en-1-one.

On the other hand, graminaceous crops such as wheat, barley, rye, are harmed only to a minor extent, if at all, by applying esters based on esters of 3,5-dichloro-4-hydroxybenzonitrile and any of the following acids:
2-[4,5-dihydro-4-methyl-4-(1-methylethyl)-5-oxo-1H-imidazol-2-yl]-4(or 5)-methylbenzoic acid,
3,6-dichloro-o-anisic acid,
(2,4-dichlorophenoxy)acetic acid,
O-[5-(2-chloro-α,α,α-trifluoro-p-tolyloxy)-2-nitrobenzoyl] glycolic acid.

Weeds in maize can be controlled by applying esters based on the following acids:
(2,4-dichlorophenoxy)acetic acid,
3,6-dichloropyridine-2-carboxylic acid,
3,6-dichloro-o-anisic acid, and
4-amino-3,5-dichloro-6-fluoro-2-pyridyloxyacetic acid; and these alcohols:
6-chloro-3-phenylpyridazin-4-ol,
3,5-dibromo-4-hydroxybenzonitrile, and
3,5-dichloro-4-hydroxybenzonitrile.

For these reasons, the present compounds are highly suitable for the selective control of undesired vegetation in stands of agriculturally useful plants or of ornamentals.

They are also suitable for generally controlling and inhibiting undesired vegetative growth without destroying the plants in the process. Inhibition of the vegetative growth plays an important role in many monocotyledonous and dicotyledonous crops since lodging can be reduced, or prevented completely, thereby.

Owing to their herbicidal and plant-growth regulatory properties, the herbicidal combinations according to the invention can also be employed for controlling harmful plants in crops of genetically modified plants which are known or yet to be developed. As a rule, the transgenic plants are distinguished by particular advantageous properties, in particular, by resistances to certain pesticides, especially certain herbicides.

In the case of application to pesticide-resistant crops, the more useful herbicidal compounds in the present invention are designed by creating esters with herbicidal acids and/or alcohols to which the crop is naturally or genetically resistant. The combined effect of the various acids at different cellular targets effectively reduces or eliminates any possible resistant weed species and/or prevents the development of such resistant strains.

The use of the compositions according to the invention in economically important transgenic crops of useful plants and ornamentals, such as graminaceous crops such as wheat, barley, rye, oats, millet, rice and maize or else crops of sugarbeet, cotton, soybean, oilseed rape, potato, tomato, pea and other vegetables is preferred. The compositions according to the invention may preferably be employed as herbicides in crops of useful plants which are resistant to the phytotoxic effects of the herbicides or which have been rendered resistant to the phytotoxic effects of the herbicides by recombinant means.

When the herbicidal compositions according to the invention are used in transgenic crops, effects are frequently observed—in addition to the effects on harmful plants which can be observed in other crops—which are specific for the application in the transgenic crop in question, for example a modified or specifically extended weed spectrum which can be controlled.

Another object of the invention is therefore the use of the compositions according to the invention as herbicides for controlling harmful plants, preferably in crops of plants, it also being possible for the crops of plants to take the form of crops of transgenic plants.

The herbicidal compositions according to the invention can also be employed non-selectively for controlling undesired vegetation, for example in plantation crops, on verges, squares, industrial terrain or rail tracks.

In a preferred method variant, the herbicides are applied in application rates of from 0.1 to 2000 g of active substances/ha, preferably of from 0.5 to 1000 g of active substances/ha. It is furthermore especially preferred to apply the active ingredients in the form of a ready-mix or in the form of tank mixes, where the individual components, for example in the form of formulations, are jointly mixed with water in the tank and the resulting spray mixture is applied.

The herbicidal compositions according to the invention can be applied in the customary fashion, for example with water as carrier in spray mixture quantities of approximately 5 to 4000 liters/ha. Application of the compositions by what is known as the low-volume and ultra-low-volume methods (ULV) is also possible, as is their application in the form of granules and microgranules.

This results in a large number of possibilities of combining several active substances with each other and of employing them jointly for controlling harmful plants in crops of plants without deviating from the spirit of the invention.

Thus, in a preferred embodiment, for example various active substances of the formula (I) and/or their salts may be combined with each other.

In conclusion, it can be said that the herbicidal compositions according to the invention have an outstanding herbicidal action and that in a preferred embodiment selectivity to useful crops is observed.

The abovementioned properties are required in weed control practice in order to keep agricultural crops free from undesired plant competitors and thus to safeguard and/or increase the yields in terms of quality and quantity. The current invention allows the user to attain a new level of broad-spectrum weed control as well as high selectivity with reduced appearance of weed resistance. Thus, a considerably improved reliability of action is observed under different environmental conditions.

The invention will now be described with reference to a number of specific examples that are to be regarded solely as illustrative of the compositions of this invention and not as restrictive of the scope thereof.

EXAMPLE 1

6-chloro-3-phenylpyridazin-4-yl 4-[hydroxyl(methyl) phosphinoyl]-DL-alaninate is active against broad leaved weeds and grasses when applied in an aqueous solution at 500-2000 ppm and is selective to glufosinate-resistant corn.

EXAMPLE 2

2,3,5-trichloropyridin-4-yl 4-[hydroxyl(methyl)phosphinoyl]-DL-alaninate is a powerful non-selective herbicide, active against broad leaved weeds and grasses when applied in an aqueous solution at 500-2000 ppm.

What is claimed is:

1. A compound of the formula:

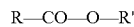

wherein RCOO is an acetate of an aryloxyphenoxypropionic acid and R' is the respective group of a 3,5-dihalo-4-hydroxybenzonitrile alcohol wherein the halogens are selected from the group consisting of iodine, bromine and chlorine.

2. A compound of the formula:

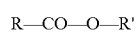

wherein RCOO is an acetate of RS(-2-[4-(4-chlorophenoxy)phenoxy]propionic acid) and R' is the respective group of the 3,5-dichloro-4-hydroxy benzonitrile alcohol.

3. A composition suitable for controlling the growth of unwanted vegetation which comprises an effective amount of a compound of claim 1 at least one surfactant, solid diluent, liquid diluent, or a mixture thereof.

4. A composition suitable for controlling the growth of unwanted vegetation which comprises an effective amount of a compound of claim 2 and at least one surfactant, solid diluent, liquid diluent, or a mixture thereof.

* * * * *